United States Patent
Khalili et al.

[11] Patent Number: 6,027,503
[45] Date of Patent: Feb. 22, 2000

[54] ORTHOPEDIC REAMING INSTRUMENT

[75] Inventors: Farid Bruce Khalili, Chestnut Hill; Robert E. Sommerich, Norton; Pierre S. Ostiguy, Rochester; Alan Cornell, Franklin, all of Mass.

[73] Assignee: Johnson & Johnson Professional, Inc., Raynham, Mass.

[21] Appl. No.: 08/954,327

[22] Filed: Oct. 17, 1997

[51] Int. Cl.[7] ................................................. A61B 17/56
[52] U.S. Cl. ................................................................ 606/81
[58] Field of Search ............................. 606/81, 80, 79, 606/85, 89, 87, 86; 623/22, 23

[56] References Cited

U.S. PATENT DOCUMENTS

| 3,412,733 | 11/1968 | Rose | 606/81 |
|---|---|---|---|
| 3,630,204 | 12/1971 | Fishbein | 606/81 |
| 4,695,282 | 9/1987 | Forte et al. | 623/22 |
| 4,704,127 | 11/1987 | Averill et al. | 623/22 |
| 4,892,549 | 1/1990 | Figgie, III et al. | 623/22 |
| 5,116,165 | 5/1992 | Salyer | 407/54 |
| 5,358,532 | 10/1994 | Evan et al. | 623/22 |
| 5,549,701 | 8/1996 | Mikhail | 623/22 |
| 5,571,201 | 11/1996 | Averill et al. | 62/22 |
| 5,755,719 | 5/1998 | Frieze et al. | 606/81 |

FOREIGN PATENT DOCUMENTS

| 94 05967 | 5/1994 | France . |
|---|---|---|
| 74 04362 | 8/1997 | France . |
| 97/19656 | 6/1997 | WIPO . |

*Primary Examiner*—Michael Buiz
*Assistant Examiner*—David O. Reip
*Attorney, Agent, or Firm*—Nutter, McClennen & Fish LLP

[57] ABSTRACT

An orthopedic reaming instrument has an elongate member and a reaming member disposed on a distal end of the elongate member. The reaming member includes a distal apical region in the form of a partial sphere having an arc of less than 180° and a proximal cylindrical region. An acetabular instrumentation system has an acetabular prosthesis in the form of a partial sphere having an arc of less than or equal to 180° and an acetabular reamer which includes a distal apical region in the form of a partial sphere having an arc that is less than the arc of the prosthesis.

16 Claims, 2 Drawing Sheets

ORTHOPEDIC REAMING INSTRUMENT

CROSS-REFERENCE TO RELATED APPLICATION

Not Applicable.

STATEMENT REGARDING FEDERALLY SPONSORED RESEARCH

Not Applicable.

FIELD OF THE INVENTION

The invention relates to implantable prostheses, and more particularly to instrumentation for the implantation of an acetabular shell.

BACKGROUND OF THE INVENTION

The hip joint is a ball-and-socket type joint in which the ball-shaped femoral head is engaged with and articulates with a cup-shaped socket known as the acetabulum. Injury or disease may damage the hip joint to the extent that it must be replaced by or augmented with a prosthetic joint. Deterioration of the acetabulum, and particularly the cartilage within the acetabulum, requires that a prosthetic acetabular shell be mounted within a prepared area of the acetabulum. The acetabular shell receives and articulates with a prosthetic femoral head which extends from a femoral stem that is installed within a proximal portion of a patient's femur.

A successful hip replacement or arthroplasty procedure results, in part, from selection of prosthetic joint components that are dimensioned and positioned to closely approximate the geometry and functional characteristics of a natural, healthy hip joint. A successful arthroplasty procedure also requires a strong attachment between the prosthetic devices and the patient's bone at the time of implantation and throughout the life of the prosthesis. Successful attachment of the acetabular shell to the patient's acetabulum is critical to a successful arthroplasty procedure.

Generally, acetabular shells are hemispherical cups that are secured within a patient's prepared acetabulum by an interference fit, mechanical attachment devices or adhesives such as bone cement. Bone cement provides good attachment qualities upon implantation of the acetabular shell, but the attachment can deteriorate over time. Under repeated loading, the cement can fatigue and fracture, resulting in loosening of the prosthesis and the formation of debris within and around the prosthesis. Loosening of the prosthesis is obviously problematic because removal and replacement of a loosened acetabular shell may result in the loss of a great deal of natural bone as the cement is removed from the patient's acetabulum.

Mechanical fixation of acetabular shells, using screws or similar mechanical fixation devices, is often effective but not always preferred. Factors such as the availability of bone of sufficient strength and quality and the proximity of arteries limit the application and effectiveness of the mechanical fixation devices.

Conventional methods for implanting acetabular shells also include the use of an interference fit between the prosthetic acetabular shell and bone. One such method involves reaming a spherical cavity in the patient's acetabulum and forcibly inserting therein a hemispherical acetabular shell having a radius that is greater than that of the reamed cavity. As a result of the greater size of the acetabular shell, an interference fit is created between acetabular shell and the patient's acetabulum. Generally, such an oversized acetabular shell is retained within the acetabulum by horizontal forces applied about the peripheral edge of the shell by interference with the smaller acetabular opening. However, vertical reactive forces are also applied in the apical region of the hemispherical shell. These vertical forces can make it difficult to optimally seat and retain the shell within the acetabulum.

Other known acetabular shells employ a so-called "dual radius" or "dual geometry." One such device, described in U.S. Pat. No. 4,704,127, is an acetabular shell that has a hemispherical shape with a frustro-conical surface portion which protrudes radially outward in proximity to the periphery of the hemisphere, providing the shell with a stepped exterior surface. The acetabulum is prepared by reaming to create a spherical portion having the same radius as the spherical portion of the shell. Separately, a frustro-conical portion is reamed having a smaller radius than the frustro-conical surface portion of the shell. When the shell is inserted into the prepared acetabulum, an interference fit is created at the interface of the differently sized frustro-conical surface portions. While this embodiment eases some of the disadvantages of the prior methods, the two-step reaming process increases the complexity of the operation and instrumentation and may result in a less precise fit. This process also requires removal of additional amounts of the patient's bone. For obvious reasons, it is preferred to remove less rather than more of the healthy portions of the patient's bone when implanting orthopedic prostheses.

A further example of an acetabular shell adapted for interference fixation is provided in U.S. Pat. No. 4,892,549. This acetabular shell is generally hemispherical, having an apical spherical region with a first radius and a peripheral spherical region with a second, larger radius resulting in a stepped outer surface. Such an acetabular shell is implanted within an acetabulum that is prepared by reaming spherically at a radius approximately equal to the radius of the apical spherical region of the shell. An interference fit is thus created at the interface of the larger peripheral spherical region of the shell with the acetabulum.

Each of the acetabular shells described above requires a unique prosthesis part which must be kept in inventory in a variety of sizes. Furthermore, this inventory must be kept in proximity to the operating environment to allow the orthopedic surgeon to select the best implantation technique depending on factors such as bone consistency and quality that are revealed only during implantation surgery.

Accordingly, there is need for acetabular instrumentation that removes smaller amounts of the patient's bone, provides for a high quality interference fit with the portions of the acetabulum where the bone is strongest, and allows surgeons the option to vary the amount of interference and the method of implantation during surgery without increasing prosthesis inventory.

SUMMARY OF THE INVENTION

The present invention provides an orthopedic instrument for reaming a patient's bone to receive a prosthesis. The instrument of the invention has an elongate member and a reaming member disposed on a distal end of the elongate member. The reaming member includes a distal apical region in the form of a partial sphere having an arc of less than 180° and a proximal peripheral edge. The reaming member further includes a proximal cylindrical region having a distal circumferential edge that is contiguous with the proximal peripheral edge of the partial sphere. The reaming member has an outer bone contacting surface which may include cutting teeth on at least a portion thereof.

An orthopedic instrument of the invention may also be part of an acetabular instrumentation system including an acetabular prosthesis and an acetabular reamer. In this embodiment, the acetabular prosthesis may be a partial sphere which spans an arc that is less than or equal to 180°—that is, it is a spherical portion smaller than a hemisphere. The acetabular reamer has an element, such as a handle, for transmitting rotational motion and a reaming member disposed on a distal end of the rotation transmitting element. The reaming member is in the form of a partial sphere having an outer bone contacting surface. The spherical portions of the prosthesis and the reaming member have equal radii, but the partial sphere of the reaming member spans a smaller arc than that spanned by the partial sphere of the prosthesis.

The present invention further provides a method for inserting an acetabular prosthesis. The method first provides an acetabular prosthesis having a hemispherical outer surface and an acetabular reamer. The acetabular reamer has an elongate member and a reaming member disposed on a distal end of the elongate member. The reaming member is in the form of a partial sphere having an arc of less than 180°. A surgeon prepares a cavity in an acetabulum for receipt of the acetabular prosthesis by applying the acetabular reamer to a depth approximately equal to the depth to a seating depth of the acetabular prosthesis. The surgeon then inserts the acetabular prosthesis into the prepared acetabulum so that the prosthesis is fully seated within the acetabulum and retained therein by an interference fit at least between a peripheral ridge of the cavity and the acetabular prosthesis.

BRIEF DESCRIPTION OF THE DRAWINGS

The invention will be more fully understood by reference to the following detailed description when considered in conjunction with the accompanying drawings, in which.

DETAILED DESCRIPTION OF THE INVENTION

Figure 1:
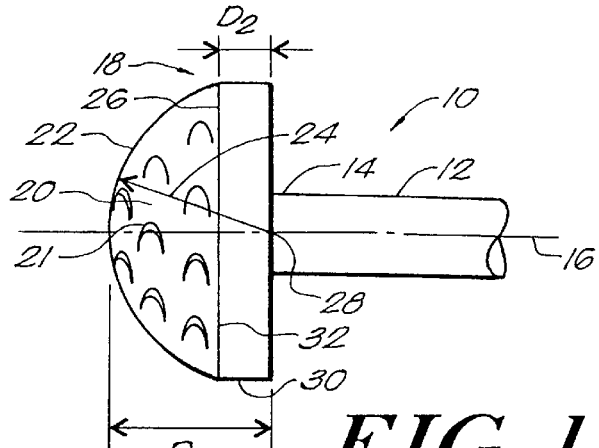
FIG. 1 is a side view of an orthopedic reaming instrument of the invention.
Figure 2:
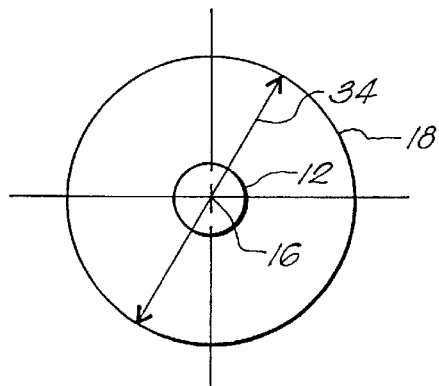
FIG. 2 is an end view of the orthopedic reaming instrument of FIG. 1.

An orthopedic reaming instrument 10, shown in FIGS. 1 and 2, has an elongate member 12 having a proximal end (not shown), a distal end 14 and a longitudinal axis 16. A reaming member 18 having an outer bone contacting surface 20 is disposed on the distal end 14 of the elongate member 12 and has a depth $D_1$.

Figure 2A:
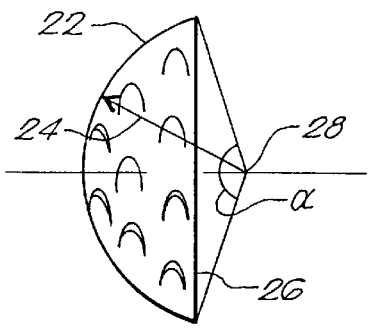
FIG. 2A is a side view of a distal apical portion of the orthopedic reaming instrument of FIG. 1.

The reaming member 18 includes a distal apical region 22 in the form of a partial sphere having an arc of less than 180°, which preferably is between about 120° and 175°. The distal apical region 22 also has a radius 24 and a proximal peripheral edge 26. The distal apical region 22, having an arc of less than 180°, necessarily constitutes less than a complete hemisphere. Accordingly, the radius 24 extends from a center of curvature 28 that is located outside the apical region 22. The arc of less than 180° is illustrated in FIG. 2A which shows a side view of the distal apical region 22 only. The radius 24 describes the surface of the distal apical region 22 by spanning an arc of angle $\alpha$. One of ordinary skill in the art will readily observe that the angle $\alpha$ is less than 180° for the embodiment shown in FIGS. 1 to 2A.

The reaming member 18 further includes a proximal cylindrical region 30 having a depth $D_2$. A distal circumferential edge 32 of the cylindrical region 30 is contiguous with the proximal peripheral edge 26 of the apical region 22.

Cutting teeth 21 are provided on at least a portion of the outer bone contacting surface 20. Preferably, cutting teeth 21 are disposed only on the portion of the outer bone contacting surface 20 corresponding to the distal apical region 22. Region 30 may be designed so that it would not remove any bone during reaming.

Generally, the depth $D_1$ of the reaming member 18 is between about 18 to 40 mm. The depth $D_2$ of the cylindrical region 30 may make up approximately one third of the reaming member depth $D_1$ and is preferably in the range of about 6 to 15 mm. In the embodiment shown in FIG. 1, the depth $D_1$ of the reaming member 30 is approximately equal to the radius 24 of the apical region 22. The reaming member 18 thus has a depth $D_1$ equivalent to the depth of a hemisphere having a radius equal to $D_1$, but has a smaller diameter 34 at its periphery than such a hemisphere. Generally, the diameter 34 is approximately 33 to 80 mm.

Figure 3:
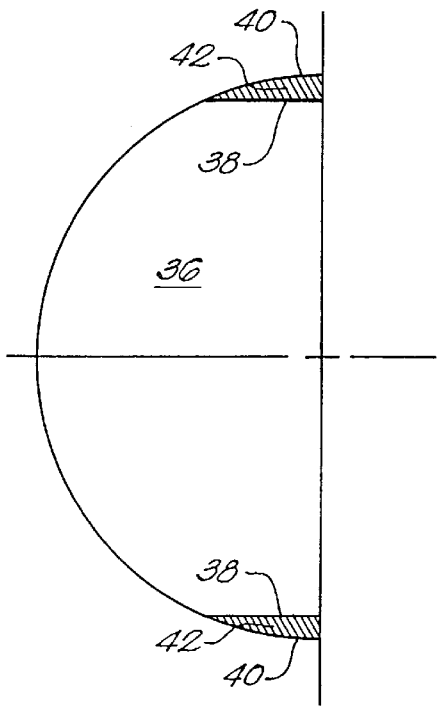
FIG. 3 is a cross sectional view of a cavity formed using the orthopedic reaming instrument of FIG. 1.

FIG. 3, which shows the shape of a cavity 36 formed by the orthopedic reamer 10 in an acetabulum, illustrates the difference between the shape of the reaming member 18 and a hemisphere. The inner outline 38 marks the shape of the cavity 36 formed in the acetabulum by reaming with the reamer 10. The outer outline 40 marks the shape of a hemisphere. When a hemispherical acetabular cup is inserted into the cavity 36, the bone cavity 36 assumes the hemispherical shape of the outer outline 40 as it is deformed by the force exerted by press-fitting the acetabular cup into the cavity 36. An interference fit is thus created between the bone cavity 36 and the acetabular cup around the periphery of the cavity 36 in the region 42 where the bone is deformed.

One of ordinary skill in the art will recognize that other configurations of the orthopedic reaming instrument are possible within the scope of the invention. For example, the acetabular prosthesis might not take the form of a complete hemisphere, but that of a partial sphere that is smaller than a hemisphere. Under these circumstances, the distal apical region of the orthopedic reaming instrument should have a radius equal to that of the acetabular prosthesis, and should be in the form of a partial sphere having an arc less than that of the acetabular prosthesis. In addition, the depth of the orthopedic reaming device, or more importantly the depth to which the reaming device is employed to create a cavity for the acetabular prosthesis, should be equal to the depth of the acetabular prosthesis.

Figure 4:
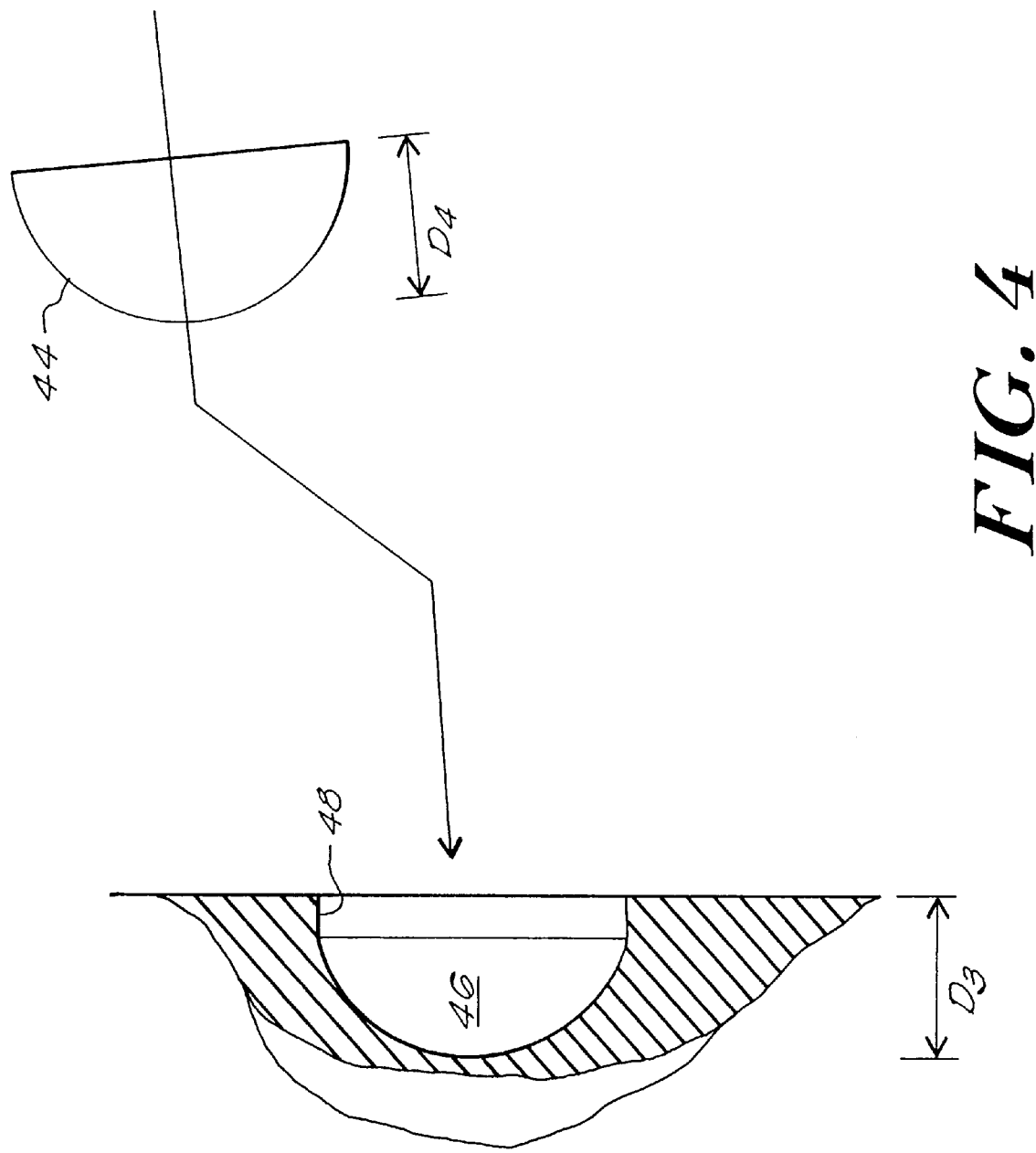
FIG. 4 is a diagram illustrating a method for inserting an acetabular prosthesis using the orthopedic reaming instrument of the invention.

The orthopedic reaming instrument 10 may be used in the following method, illustrated in FIG. 4, to implant an acetabular prosthesis 44. The elongate member 12 of the reaming instrument 10 may be removably engaged with a device which transmits rotational motion, such as a drill, so that the reaming instrument 10 is rotated about its longitudinal axis 16. A surgeon then lines up the reaming instrument 10 with the acetabulum being prepared for receipt of the prosthesis 44, and prepares a cavity 46 by reaming to a depth $D_3$ approximately equal to the seating depth $D_4$ of the acetabular prosthesis 44. The surgeon then inserts the acetabular prosthesis 44 into the prepared cavity 46 so that the prosthesis 44 is fully seated within the acetabulum and is retained therein by an interference fit at least between a peripheral ridge 48 of the cavity 46 and the acetabular prosthesis 44.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. An orthopedic reaming instrument comprising:
   an elongate member having proximal and distal ends and a longitudinal axis; and
   a reaming member disposed on the distal end of the elongate member, the reaming member having a depth of about 18 to 40 mm and an outer bone contacting surface and including:
      a distal apical region in the form of a partial sphere having an arc of between 120° and 175°, a radius and a proximal peripheral edge; and
      a proximal cylindrical region having a depth of between 6 and 15 mm and a distal circumferential edge adjacent to the proximal peripheral edge of the distal apical region.

2. The instrument of claim 1, wherein the depth of the reaming member is approximately equal to the radius of the partial sphere.

3. The instrument of claim 1, wherein the proximal cylindrical region has a depth of approximately one-third of the depth of the reaming member.

4. The instrument of claim 1, wherein the diameter of the instrument is approximately 33 to 80 mm.

5. The instrument of claim 1, wherein the instrument is rotatable about the longitudinal axis of the elongate member.

6. The instrument of claim 1, wherein at least a portion of the outer bone contacting surface includes cutting teeth.

7. The instrument of claim 6, wherein the cutting teeth are formed on only the outer surface of the distal apical region.

8. An acetabular instrumentation system including:
   an acetabular prosthesis comprising a partial sphere having a radius and spanning a prothesis arc that is less than or equal to 180°; and
   an acetabular reamer comprising:
      a means for transmitting rotational motion having proximal and distal ends and a longitudinal axis; and
      a reaming member disposed at the distal end of the means for transmitting rotational motion, the reaming member being in the form of a partial sphere having an outer bone contacting surface with a distal apex and a proximal peripheral edge, the partial sphere having a reamer arc that is less than the prosthesis arc and having a radius that is approximately equal to the radius of the acetabular prosthesis.

9. The system of claim 8, wherein the reaming member has a radius of about 18 to 40 mm.

10. The system of claim 8, wherein the outer bone contacting surface includes cutting teeth.

11. The system of claim 8, wherein the acetabular prosthesis is in the form of a hemisphere.

12. The system of claim 8, wherein the partial sphere has a reamer arc of between about 120° and 175°.

13. A method for inserting an acetabular prosthesis comprising the steps of:
   providing an acetabular prosthesis having a longitudinal depth and comprising a partial sphere having a radius and spanning a prosthesis arc that is less than or equal to 180°;
   providing a dual geometry acetabular reamer comprising:
      an elongate member having proximal and distal ends; and
      a reaming member disposed at the distal end of the elongate member, the reaming member being in the form of a partial sphere spanning a reamer arc that is less than the prosthesis arc, the partial sphere having a radius approximately equal to the radius of the acetabular prosthesis, a distal apical region and a proximal peripheral edge;
   preparing a cavity in an acetabulum for receipt of the acetabular prosthesis by applying the dual geometry acetabular reamer to the acetabulum to a reaming depth; and
   inserting the acetabular prosthesis into the prepared acetabulum so that the prosthesis is fully seated within the acetabulum and retained therein by an interference fit at least between a peripheral ridge of the cavity and the acetabular prosthesis.

14. The method of claim 13, wherein the reaming member further comprises a proximal cylindrical region having a distal circumferential edge adjacent to the proximal peripheral edge of the partial sphere, and a proximal circumferential edge.

15. The method of claim 13, wherein the reaming depth is approximately equal to the longitudinal depth of the acetabular prosthesis.

16. The method of claim 13, wherein the reaming member partial sphere spans an arc of between about 120° and 175°.

* * * * *